United States Patent [19]
Merchant et al.

[11] Patent Number: 6,165,541
[45] Date of Patent: Dec. 26, 2000

[54] GEL-TEMPLATE INTERFACE AND METHOD FOR DEPOSITING LIQUID ON A GEL

[75] Inventors: Mark E. Merchant, Nederland; Philip A. Guadagno, Vidor; Suzan Robinson, Beaumont, all of Tex.

[73] Assignee: Helena Laboratories Corporation, Beaumont, Tex.

[21] Appl. No.: 09/301,622

[22] Filed: Apr. 29, 1999

[51] Int. Cl.[7] ............... B05D 1/26; B05D 1/32; G01N 21/01; C12N 11/12
[52] U.S. Cl. ............... 427/2.11; 427/2.13; 427/4; 427/272; 356/244; 222/462; 435/179
[58] Field of Search ............... 427/2.11, 2.13, 427/2.3, 4, 259, 272, 282, 284; 435/287.2, 179, 809; 356/244, 40; 222/462

[56] References Cited
U.S. PATENT DOCUMENTS

| | | | |
|---|---|---|---|
| 3,844,918 | 10/1974 | Cawley | 204/180 G |
| 3,990,852 | 11/1976 | Piazzi et al. | 23/253 R |
| 4,668,363 | 5/1987 | Gebott et al. | 204/182.8 |
| 5,100,626 | 3/1992 | Levin | 422/100 |
| 5,137,614 | 8/1992 | Golias | 204/199 R |
| 5,403,456 | 4/1995 | Bellon | 427/2.11 |

*Primary Examiner*—Shrive Beck
*Assistant Examiner*—Jennifer Kolb
*Attorney, Agent, or Firm*—Arter & Hadden LLP

[57] ABSTRACT

An improvement in the immunofixation electrophoresis procedure for detecting proteins in serum, urine or cerebral spinal fluids. Samples are placed on a gel and subjected to electrophoresis for resolving or separating proteins. Thereafter, antisera are applied to the sample areas through openings located on a template. The template includes projections and, the template substantially precludes cross-contamination and the adverse effects of ambient conditions on the integrity of the fluid, such as by the projections contacting, depressing or cutting into the gel to form closed cavities.

30 Claims, 3 Drawing Sheets

GEL-TEMPLATE INTERFACE AND METHOD FOR DEPOSITING LIQUID ON A GEL

BACKGROUND ART

This invention relates to template devices and has particular utility as an antisera template in an immunofixation electrophoresis system.

Immunofixation electrophoresis, referred to as IFE, is well-known as a two-stage procedure for detecting the presence of certain proteins in human serum, urine or cerebral spinal fluid. The procedure involves, as a first step, protein fraction resolution by electrophoresis. As a second step, the soluble antigen in each protein fraction is allowed to react with its antibody. The resultant antigen-antibody complexes will precipitate, at a rate dependent upon the proportion of the reactants, temperature, salt concentration and pH. The antigen-antibody complexes are then visualized by staining.

The IFE process is described in greater detail in Gebott et al, U.S. Pat. No. 4,668,363 issued May 26, 1987, which is hereby incorporated by reference. Apparatus and chemicals for performing IFE have been marketed for some time by Helena Laboratories Corporation of Beaumont, Tex.

Typically, a specimen from a single patient is diluted and then placed in multiple sample or application areas (also referred to as zones) on a single electrophoretic gel plate. The purpose of utilizing multiple sample areas is to enable detection separately of total serum protein, and various proteins such as the immunoglobin heavy chains IgG, IgM, IgA and light chains Kappa and Lambda, or other proteins whose presence or absence may be of importance in medical diagnosis. As known in the prior art, various antisera (i.e., fluid containing the antibody) such as IgG, IgM, etc., are deposited on the appropriate zones and permitted to react with the antigen in the sample. The term "incubation" refers to the time interval during which the antisera and antibody are in contact such that a reaction may occur.

Prior to the present invention, in order to determine the effectiveness of the chemicals, various techniques were employed. U.S. Pat. No. 5,137,614, issued on Aug. 11, 1992 to Golias, which is hereby incorporated by reference, is directed to a control system including a template for verifying the effectiveness of the chemicals utilized in the immunofixation electrophoresis procedure. This is accomplished without the need to interrupt patient specimen evaluation when chemicals are replenished, since the chemical utilized on the specimens are also utilized in the control test. The control system verifies that the chemicals have retained their lability.

U.S. Pat. No. 3,844,918, issued on Oct. 29, 1974 to Crawley, which is hereby incorporated by reference, is directed to a template which includes an aperture through which serum is received. The template is placed on a mold having an extended portion which passes through the aperture. Gel is coated on one surface of the template. When the gel molds around the portion extending through the aperture, the mold is removed from the template. The template is left with a small cavity in which the serum is placed.

U.S. Pat. No. 5,403,456, issued on Apr. 4, 1995 to Bellon, which is hereby incorporated by reference, is directed to a mask which includes an orifice through which liquid is deposited on the zone of the gel, and a slit through which excess liquid is withdrawn from the zone of the gel after the incubation step. In practice, the mask is placed in close proximity to, but spaced apart from the surface of the gel, the liquid is deposited through the mask onto the gel, the mask is maintained in its relative position during the incubation step, and, thereafter, excess liquid is withdrawn through the mask. Then, of course, the mask, is removed.

Applicants have discovered that use of the type of device described in the Bellon patent has certain drawbacks. For example, the fluid sample is exposed to ambient conditions and thus partial evaporation may occur. This will change the concentration of the sample and affect quantitative analysis. Similarly, the antisera are exposed to ambient conditions during incubation, again leading to partial evaporation, change in concentration, and sensitivity errors. In addition, ambient conditions may otherwise affect the integrity of the fluid.

After the electrophoretic separation step, the entire reaction zone must be covered with the antiserum since the antigen (i.e., protein fraction) resolution may have occurred virtually at any position along the reaction zone. If the entire zone is not covered, the antibody-antigen reaction may not occur; thus covering the entire zone is important for qualitative purposes. Furthermore, there must be sufficient antiserum deposited to insure that all the antigen will react, otherwise the quantitative aspect of the test will be compromised. Thus it is conventional to apply excess amounts of antiserum. However, Applicants have discovered that prior art techniques and apparatus fail to properly control the flow of the antiserum. Thus, for example, in IFE, or any other procedure, where various reagents are deposited on distinct zones of the same gel, the use of excess amounts of reagent can cause the reagent to "overflow" from one zone onto an adjacent zone. Another problem is that if the reagents in two adjacent zones each "overflow" their respective zones, the reagent which "overflows" one zone can contact the reagent which "overflows" from an adjacent zone, resulting in "cross-contamination" between zones or otherwise compromising the test results for one or more zones.

SUMMARY OF INVENTION

The present invention overcomes the difficulties and shortcomings of the prior art by providing a system that forms physical contact between the gel and a mask or template to create a gel-template interface. When the template contacts the gel, projections, which define the boundaries of the channels in the template, cut into the gel (or at least depress the surface of the gel) converting the channels into closed cavities, with the gel (or more particularly the zone on the gel) forming the base of the cavity, the projections forming the sides of the cavity, and the underside of the template forming the top of the cavity. The template preferably includes a first opening and a second opening for each channel; the first opening allows introduction and removal of liquids to and from the closed cavity and the second opening allows air to exit the cavity. The use of the closed cavities solves the aforementioned problems of the prior art.

BRIEF DESCRIPTION OF DRAWINGS

The various objects, advantages and benefits of the present invention will become more apparent upon reading the following detailed description of the invention taken in conjunction with the drawings. In the drawings.

DISCLOSURE OF INVENTION

Figure 1:
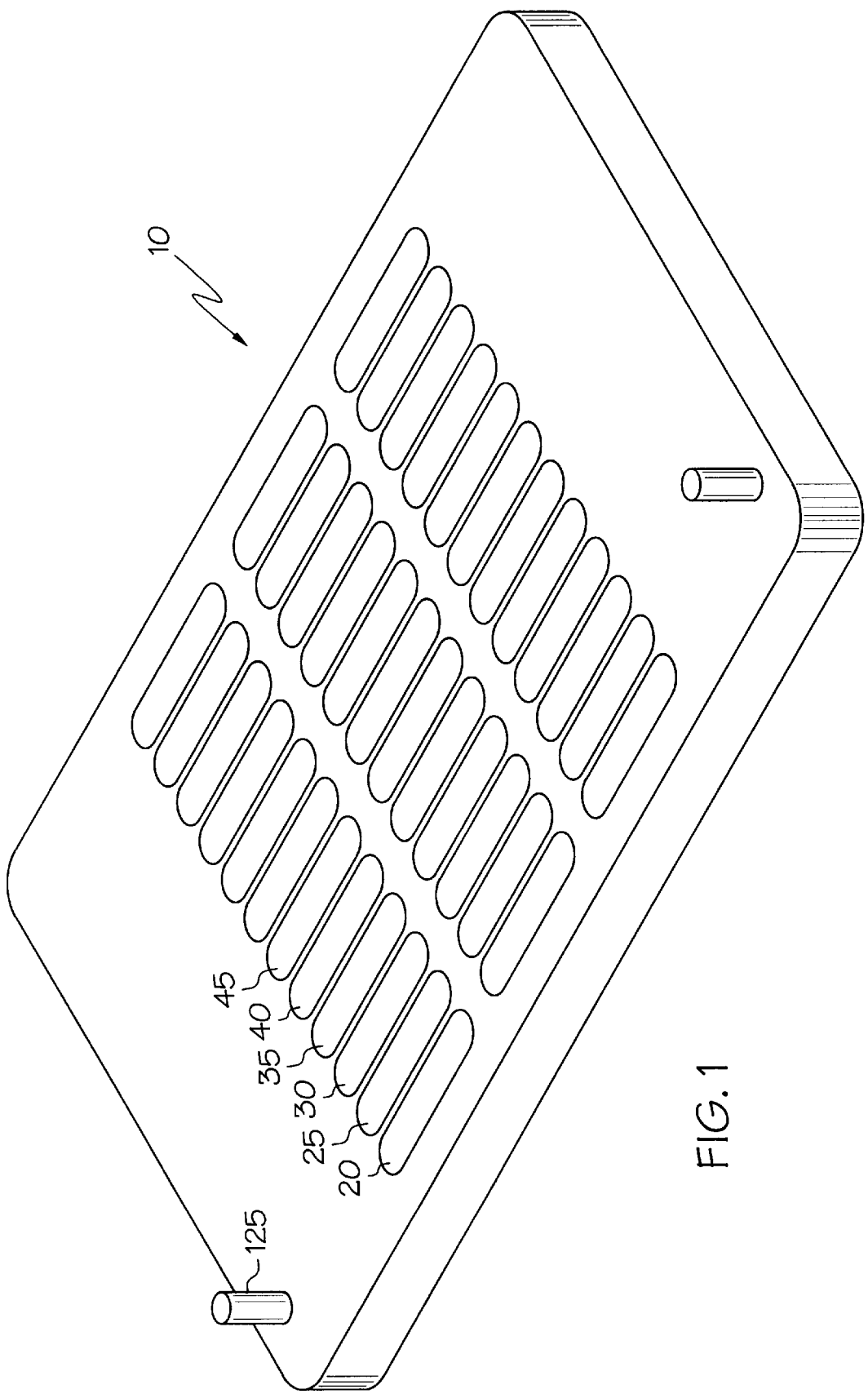
FIG. 1 is a perspective view of an electrophoresis gel plate.

The present invention is described in the non-limiting but merely illustrative context of an applicator or template for use in immunofixation electrophoresis. With reference to the drawings, an electrophoresis plate, such as an agarose gel plate 10 is illustrated in FIG. 1. The gel plate 10 is illustrated as including plural, discrete regions or zones for the application of patient samples. For illustrative purposes only, 36 zones are illustrated. These zones are arranged in three series of twelve zones each, with the zones in each series extending transversely of the length of the plate. In IFE as previously explained, it is desired to simultaneously test for six proteins (actually five proteins plus total serum protein). Thus a "sample" or specimen from a patient is typically divided into six aliquots. In the illustrated embodiment, therefore, six zones will be used to test the six aliquots from a single patient. Hence six zones have been identified with reference numerals 20, 25, 30, 35, 40 and 45, respectively. The zones are understood as regions of the gel 10 where the samples are deposited, where electrophoretic separation occurs, where the reagents are deposited and incubation occurs such that antibody-antigen reactions will occur, and where staining (for visualizing) occurs. The remaining 30 zones on the gel have been illustrated without reference numerals merely for the purpose of clarity.

Figure 2:
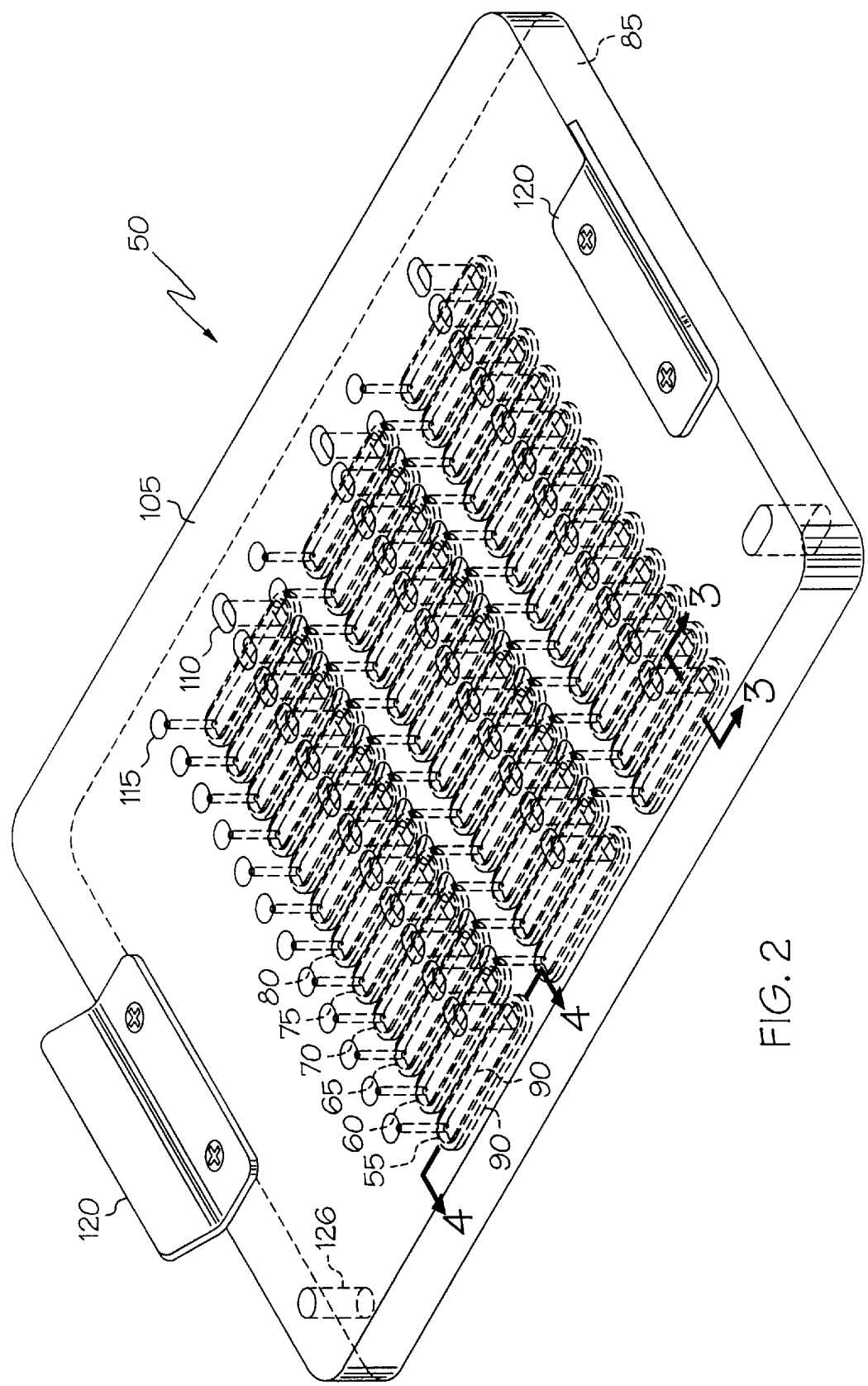
FIG. 2 is a perspective view of a template of the present invention.

FIG. 2 is a perspective view of a generally flat, generally rigid template 50 having multiple elongated channels. For illustrative purposes, the channels are arranged in three series of twelve channels each for a total of thirty-six channels. Each separation zone on the gel 10 which is to be utilized should have a corresponding channel on the template 50. To demonstrate this correspondence, therefore, since six separation zones have been identified by reference numerals on the gel plate 10 of FIG. 1, then six corresponding channels 55, 60, 65, 70, 75 and 80 are identified on the template 50. If six channels are used for IFE processing of the six aliquots from a single patient, the template 50 may be used for processing samples from one to six patients simultaneously Template 50 will now be explained in a non-limiting, illustrative context as an antisera applicator template. In use, the channels on template 50 are aligned over the corresponding electrophoresis zones of the gel plate 10. Each channel has a length approximately 1.5 mm to approximately 2.5 mm. The template 50, which is preferably transparent, has a thickness of approximately 10 mm to approximately 15 mm, and may be made of plexiglass or other nonreactive material.

The template has a lower surface 85 from which a series of projections 90 extend outwardly and, by way of example, each projection forms the perimeter of a channel. Each channel is, for illustrative purposes, generally rectangular in configuration, with generally straight sides and curved ends. Thus, for each channel, a continuous projection 90 forms the generally straight channel sides and curved channel ends. Each channel may be thought of as being formed by the generally flat lower surface 85 of the template and a corresponding projection 90, and a projection separates a channel from other channels for the purpose of limiting the flow of liquid.

The template 50 includes an upper surface 105 which is preferably smooth without any irregularities except for a plurality of first and second openings 110, 115 respectively, one of each such openings associated with each channel. The first opening 110 is located at the end of each channel for introduction and removal of liquids and the second opening 115 is located at the other end of the channel for venting air. Thus the two ends of the channels may be considered as the inlet/outlet end and vent end of the channel, respectively, corresponding to the location of the first and second openings. The first and second openings 110, 115 have an elongated or round shape. The elongated shape of the first opening 110 permits easy introduction of the reagent onto the gel 10.

Alternatively, the first opening 110 can be used to introduce the liquids onto the zones on the gel plate 10 and the second opening 115 can be used to remove the liquids with air venting from the zones on the gel plate 10 through one or both openings as necessary.

The height of the projection 90 is not constant around the perimeter of the channel; rather, the height of the projection increases gradually along the sides of the channel from the second end to the first end of the channel. Thus the height of the projection at the first end, i.e., under the first opening 110, is greater than the height of the projection at the second end of the channel, i.e., under the second opening 115. The slope of the projection 90 relative to the lower template surface 105 can be approximately 0.6°.

The gel plate 10 includes alignment pins 125. If the present invention is to be utilized in an automatic or semi-automatic system, the "floor" upon which the gel plate is positioned would include alignment pins and the gel plate would include apertures in lieu of alignment pins. In that situation, the alignment pins on the floor would extend upwardly through the apertures in the gel plate 10.

Template 50 includes handles 120 on opposite sides to facilitate movement of the template onto the gel after the electrophoretic separation step and prior to the introduction of antisera. To aid in alignment of the template channels relative to the separation zones, alignment slots 126 are provided on two corners of the template 50. The alignment pins 125 (whether part of the gel plate 10 or extending upwardly through the gel plate) extend through the slots 126 for aligning the template 50 with respect to the gel plate 10 so that each channel rests above its corresponding zone.

Figure 4:
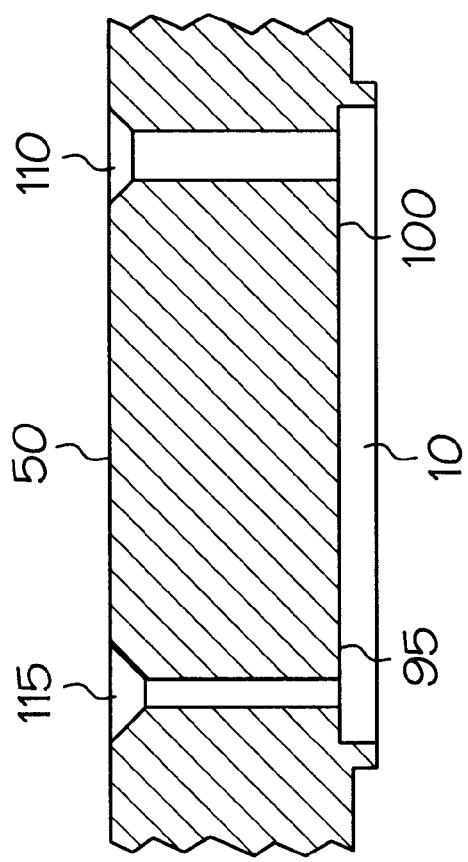
FIG. 4 is an enlarged, cross-section view of a gel-template interface as seen in the direction of arrows 4—4 of FIG. 2.
Figure 3:
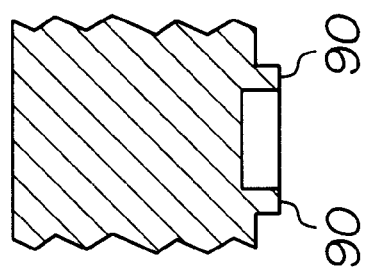
FIG. 3 is an enlarged, cross-section view of a channel on the template as seen in the direction of arrows 3—3 of FIG. 2.

FIGS. 3 and 4 illustrate a cross sectional view of a channel in contact with its corresponding zone on the gel 10 taken in the direction of arrows 3—3 and 4—4, respectively. The template 50 is positioned with respect to the gel 10 such that the projection 90 is in contact with the gel surface 10 and preferably depresses or cuts slightly into the gel 10, converting each template channel into an individual cavity which is closed except for its first 110 and second 115 openings. Thus the gel 10 (and more specifically the electrophoresis zone) forms the base for the cavity. The projection 90 preferably defines an area larger than the area of the respective zone, and thus depresses or cuts into the area surrounding the zone of the gel 10.

In operation of the present invention, after the samples have been introduced onto the separation zones of the gel, electrophoresis occurs as is conventional. Thereafter, the template 50 is placed in contact with the gel 10, with the channels of the template 50 aligned over the corresponding zones of the gel 10 and in contact with the gel 10. Sufficient pressure is applied (which can be merely the weight of the template) so that the projections 90 and gel 10 form the desired closed cavities. To accomplish this, it is preferred (but not required) that the template 50 depress the gel 10 slightly or more preferably cut into the gel slightly to form each closed cavity. Then, liquid such as a reagent (antisera)

is introduced by means of a pipette through the first opening 110 associated with each cavity. Sufficient liquid is introduced such that the liquid is distributed within the cavity to completely cover the surface of the respective zone. The deposited liquid can flow or spread within the cavity until it encounters the edges of the projection 90. The liquid is distributed or spread completely over the zone due to the downward slope of the projection 90. After the incubation step, the excess and/or unreacted liquid is removed such as through the use of filter paper, preferably through the first opening 110. In order to facilitate this removal of the liquid by filter paper, it is preferred that the lower surface 85 not be perfectly parallel to the gel 10 when in contact, but to form a dihedron with a very small angle, approximately 0.6°, the vertex of which is on the side of the second opening 115. Since the gel-template interface forms a closed cavity for each channel there is no evaporation for which extra liquid would be necessary and no cross-contamination between adjacent zones.

In the case of incubation of adjacent zones on the gel 10 with different reagents, there is sufficient contact between the gel-template interface to form the closed cavities, without there being a risk of cross-contamination between different reagents from adjacent zones. Therefore, the liquid within each closed cavity formed between the gel-template interface does not mix with the liquids kept in directly adjacent closed cavities. Moreover, the closed cavities allow for closer spacing of adjacent zones on the gel 10.

Although the present template has been described in the context of an antisera applicator for IFE, it is apparent that the invention has other uses. Furthermore it should be appreciated that all dimension are presented merely for illustrative purposes.

The purpose of the projections 90 are to contribute to the formation of closed cavities to inhibit both evaporation and cross-contamination as previously described. Depending on the duration of the incubation step, the viscosity of the reagents, the orientation of adjacent zones and numerous other factors, the principles of the present invention may be achieved by other means. By way of example and not by way of limitation, two generally straight, elongated projections may be provided on the lower surface of the template, corresponding to the sides of the channel, but no projections on the shorter "ends" of the channel. Thus two projections will be associated with each channel but the projections will not be connected to each other, i.e., the projections will be discontinuous. Projections at the "ends" of each channel may not be necessary, especially if the gel plate only has a single row of reaction zones, rather than three rows of zones as in the illustrated embodiment, thus substantially reducing, if not eliminating, the risk of cross-contamination. Furthermore, projections at the "ends" of the channel may not be necessary to reduce, if not eliminate the risk or adverse result of ambient conditions, e.g., projections (and even discontinuous projections) solely along one or both sides of a channel may be sufficient.

Many other changes and modifications may be made without departing from the spirit and scope of the present invention. The present invention, therefore, should be limited only by the following claims.

What is claimed is:

1. A gel-template interface for deposition of at least one liquid on a gel, said gel-template interface comprising:
    a gel plate;
    a template having an upper surface and a lower surface, wherein the distance separating said upper surface and said lower surface defines the thickness of said template;
    said template containing at least one first opening such that liquid introduced therethrough flows through the template to said lower surface; and
    said template lower surface including an elongated template projection extending toward and contacting the gel plate to restrict the flow of liquid on the gel.

2. The gel-template interface of claim 1, furthering comprising:
    at least one zone defined on said gel; and
    means for positioning said template with respect to said gel such that the projection contacts said gel zone at the gel-template interface.

3. The gel-template interface of claim 1, wherein a channel is defined by the lower surface of said template and said projection.

4. The gel-template interface of claim 3, wherein a cavity is formed by said channel and said zone, said cavity being closed except for said at least one first opening.

5. The gel-template interface of claim 1, including at least two openings in said template.

6. The gel-template interface of claim 5, wherein said first opening is configured for introduction of liquid to said gel and said second opening is configured for venting of air from said gel.

7. The gel-template interface of claim 1, wherein at least two zones are provided on said gel and the projection rests on the space between the zones of the gel.

8. The gel-template interface of claim 1, wherein the projection cuts slightly into the gel surface.

9. The gel-template interface of claim 1, wherein the projection of said channel slopes downward from said opening.

10. The gel-template interface of claim 1, wherein the lower surface of the template includes a plurality of spaced apart channels, and the gel includes a corresponding plurality of spaced apart zones aligned relative to said channels.

11. The gel-template interface of claim 1, wherein said projection is continuous.

12. A gel-template interface for deposition of at least one liquid on a gel, said gel-template interface comprising:
    a gel plate having at least one zone thereon;
    a template having an upper surface and a lower surface, wherein the distance separating said upper surface and said lower surface define the thickness of said template;
    said template containing at least one opening to receive liquid for deposition onto said gel; and
    said template lower surface including a projection, said template including the projection forming an elongated cavity with said zone which cavity is closed except for said opening.

13. The gel-template interface of claim 12, wherein said gel plate has a plurality of zones thereon and said template has a plurality of openings, and said template lower surface forms a cavity with each zone, each cavity being closed except for a respective opening.

14. The gel-template interface of claim 13 wherein at least one of the closed cavities includes two openings.

15. The gel-template of claim 12 wherein said template lower surface projection is continuous and cooperates with said gel to form said cavity.

16. A gel-template interface for deposition of at least one liquid on a gel, said gel-template interface comprising:
    a gel plate having at least one elongated zone thereon;
    a template having an upper surface and a lower surface, wherein the distance separating said upper surface and said lower surface defines the thickness of said template; and said template lower surface including an elongated projection cooperating with said gel to reduce the tendency of ambient conditions from affecting the integrity of said liquid.

17. The gel-template interface of claim 16 wherein said integrity of said liquid is the concentration thereof.

18. A template comprising:
an upper surface and a lower surface, wherein the distance separating said upper surface and said lower surface defines the thickness of said template;
said lower surface containing at least two elongated channels, wherein a continuous projection forms at least part of the perimeter of each channel;
said upper surface containing first and second openings associated with each elongated channel.

19. The template of claim 18, wherein said openings are located at opposite ends of each channel.

20. The template of claim 18, wherein each projection of a channel slopes downward from said first opening to said second opening.

21. The template of claim 18, wherein the height of each projection is greater at the first opening than at said second opening.

22. The template of claim 18, wherein at least one projection is coextensive with the perimeter of said channel.

23. The template of claim 18, wherein said first opening is configured for introduction and removal of said liquid relative to a channel and said second opening is configured for venting air from a channel.

24. A gel-template interface for deposition of at least one liquid on a gel, said gel-template interface comprising:
a gel plate having at least two zones thereon;
a template having an upper surface and a lower surface, wherein the distance separating said upper surface and said lower surface defines the thickness of said template;
said template upper surface containing at least one opening in fluid communication with said lower surface; and
said template lower surface having at least one projection and forming an elongated cavity with at least one zone for preventing cross-contamination between said zones.

25. A method of deposition of liquid on a gel, comprising the steps of,
positioning juxtaposed to the gel, a template having spaced apart upper and lower surfaces, said lower surface containing at least one elongated channel, said channel including at least one projection, said upper surface containing at least one opening in fluid communication with said lower surface channel;
contacting at least said template projection and gel to form an elongated cavity with the gel being the base of the cavity and the channel forming the sides and top of the cavity; and
introducing the liquid through said opening into said cavity, said cavity being closed except for said template upper surface opening.

26. The method of claim 25, further including the step of withdrawing excess liquid from said cavity through said opening.

27. The method of claim 25, wherein said template upper surface includes first and second openings, said cavity being closed except for said first and second openings, and further including the step of, withdrawing excess liquid from said cavity through at least one of said openings.

28. The method of claim 27, further including the step of venting air from said cavity through said second opening.

29. A method of deposition of liquid on a gel comprising the steps of,
positioning juxtaposed to the gel, a template having spaced apart upper and lower surfaces, said lower surface containing at least one elongated channel, said channel including a projection, said upper surface containing at least one opening;
contacting at least said template projection and gel to form an elongated cavity with the gel being the base of the cavity and the channel forming the sides and top of the cavity;
introducing the liquid through said opening into said cavity onto said gel; and
said cavity for reducing the tendency of ambient conditions from affecting the integrity of said liquid.

30. A method of deposition of liquid on a gel, comprising the steps of,
positioning juxtaposed to the gel having at least two zones thereon, a template having spaced apart upper and lower surfaces, said lower surface containing at least one elongated channel, said channel including at least one projection associated therewith, said upper surface containing at least one opening;
contacting at least said template projection and gel to form a cavity relative to at least one zone with the gel being the base of the cavity and the channel forming the sides and top of the cavity;
introducing the liquid through said opening into said cavity onto said gel; and
said cavity for reducing cross-contamination of liquid between said zones.

* * * * *